United States Patent
Sinha et al.

(10) Patent No.: US 10,241,337 B2
(45) Date of Patent: Mar. 26, 2019

(54) TUNABLE SPECTRAL SLICER AND METHODS OF USE

(71) Applicant: Verily Life Sciences LLC, Mountain View, CA (US)

(72) Inventors: Supriyo Sinha, Menlo Park, CA (US); Cheng-Hsu Wu, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 34 days.

(21) Appl. No.: 15/481,409

(22) Filed: Apr. 6, 2017

(65) Prior Publication Data

US 2017/0343825 A1 Nov. 30, 2017

Related U.S. Application Data

(60) Provisional application No. 62/342,270, filed on May 27, 2016.

(51) Int. Cl.
*G02B 27/10* (2006.01)
*G01J 3/02* (2006.01)
(Continued)

(52) U.S. Cl.
CPC ............ *G02B 27/1006* (2013.01); *G01J 3/02* (2013.01); *G01J 3/12* (2013.01); *G01J 3/2823* (2013.01);
(Continued)

(58) Field of Classification Search
CPC .. G02B 27/1006; G02B 27/10; G02B 27/141; G02B 5/20
(Continued)

(56) References Cited

U.S. PATENT DOCUMENTS

| 5,591,981 A | 1/1997 | Heffelfinger et al. |
| 6,403,947 B1 * | 6/2002 | Hoyt ............ B82Y 10/00 250/226 |

(Continued)

FOREIGN PATENT DOCUMENTS

| EP | 0916981 A1 | 5/1999 |
| EP | 2720075 A1 | 4/2014 |

(Continued)

OTHER PUBLICATIONS

Qing Ye et al., "High-efficiency electrically tunable phase diffraction grating based on a transparent lead magnesium niobate-lead titanite electro-optic ceramic", Optics Letters, Optical Society of America, vol. 36, No. 13, Jul. 1, 2011, pp. 2453-2455.

(Continued)

*Primary Examiner* — William R Alexander
(74) *Attorney, Agent, or Firm* — McDonnell Boehnen Hulbert & Berghoff LLP

(57) ABSTRACT

Systems and methods for filtering an optical beam are described. In one implementation, a system for filtering an input optical beam includes a first beamsplitter, a first spectral slicing module, a second spectral slicing module, and a second beamsplitter. The first beamsplitter is configured to split the input optical beam into a first optical beam and a second optical beam. The first spectral slicing module has a first passband and is configured to filter the first optical beam. The second spectral slicing module has a second passband and is configured to filter the second optical beam. The second beamsplitter is configured to combine the first optical beam and the second optical beam into an output optical beam. The first and second spectral slicing modules may each comprise a longpass filter and a shortpass filter aligned along its optical axis, and the longpass filter and/or the shortpass filter are rotatable relative to the optical axis. Advantageously, the optical system allows for tunable spec- (Continued)

tral filtering of the input optical beam suitable for 2-D imaging systems.

20 Claims, 6 Drawing Sheets

(51) Int. Cl.

| | |
|---|---|
| *G01J 3/12* | (2006.01) |
| *G01J 3/28* | (2006.01) |
| *G01N 21/31* | (2006.01) |
| *G02B 21/00* | (2006.01) |
| *G01N 21/64* | (2006.01) |
| *G02B 5/20* | (2006.01) |
| *G02B 27/14* | (2006.01) |
| *G02B 26/00* | (2006.01) |

(52) U.S. Cl.
CPC ......... *G01N 21/31* (2013.01); *G01N 21/6456* (2013.01); *G02B 5/20* (2013.01); *G02B 21/0064* (2013.01); *G02B 26/007* (2013.01); *G02B 27/10* (2013.01); *G02B 27/102* (2013.01); *G02B 27/141* (2013.01); *G01J 2003/1213* (2013.01); *G01N 21/6458* (2013.01)

(58) Field of Classification Search
USPC ....................................................... 359/634
See application file for complete search history.

(56) References Cited

U.S. PATENT DOCUMENTS

| | | | |
|---|---|---|---|
| 8,351,026 B2* | 1/2013 | Stern | ................. G01N 21/6428 356/73 |
| 2009/0309049 A1 | 12/2009 | Van Dijk et al. | |
| 2010/0314554 A1 | 12/2010 | Galimberti et al. | |
| 2011/0228267 A1 | 9/2011 | Hayashi | |
| 2012/0069344 A1 | 3/2012 | Liu | |
| 2012/0307247 A1 | 12/2012 | Tan et al. | |
| 2013/0100525 A1 | 4/2013 | Chiang et al. | |
| 2013/0329270 A1 | 12/2013 | Nielsen et al. | |
| 2016/0202178 A1 | 7/2016 | Acosta | |
| 2017/0089837 A1 | 3/2017 | Matsumoto et al. | |
| 2017/0176338 A1* | 6/2017 | Wu | .......................... G06T 7/90 |
| 2017/0343477 A1* | 11/2017 | Santori | ................ A61B 5/0071 |

FOREIGN PATENT DOCUMENTS

| | | |
|---|---|---|
| GB | 859208 A | 1/1961 |
| JP | S52014417 A | 2/1977 |
| JP | S63101818 A | 5/1988 |
| JP | 2015219501 A | 12/2015 |
| WO | 2016115018 A1 | 7/2016 |

OTHER PUBLICATIONS

Yanli Zhang et al., "High-efficiency, liquid-crystal-based, controllable diffraction grating", Journal of the Optical Society of America, vol. 22, No. 11, Nov. 2005, p. 2510.
Sirleto L. et al., "Electro-Optical Switch and Continuously Tunable Filter Based on a Bragg Grating in a Planar Waveguide With a Liquid Crystal Overlayer", Optical Engineering, Soc. of Photo-Optical Instrumentation Engineers, vol. 41, No. 11, Nov. 2002, pp. 2890-2898.
International Search Report of International Application No. PCT/US2016/067684 dated Mar. 9, 2017.
International Search Report of International Application No. PCT/US2017/027510 dated Jul. 7, 2017.
Favreau et al., "Thin-film tunable filters for hyperspectral fluorescence microscopy", Journal of Biomedical Optics, vol. 19(1), Jan. 2014.
"Optical Spectral Filters and Gratings", Chapter 4, pp. 71-89.
Erdogan, PhD., "Optical Filters: Tunable Filters", Semrock, a Unit of IDEX Corporation, May 31, 2011.
Anderson et al., "Angle-Tuned Thin-Film Interference Filters for Spectral Imaging", OPN Optics & Photonics News, pp. 12-13, Jan. 2011.
Erodogan, Ph.D. et al., "Semrock White Paper Series: Semrock VersaChrome, The First Widely Tunable Thin-film Optical Filters", Semrock, A Unit of IDEX.
International Search Report of International Application No. PCT/US2017/034875 dated Aug. 21, 2017.
International Search Report of International Application No. PCT/US2017/034877 dated Aug. 17, 2017.

* cited by examiner

TUNABLE SPECTRAL SLICER AND METHODS OF USE

CROSS-REFERENCE TO RELATED APPLICATIONS

This application claims the benefit of and incorporates by reference the content of U.S. Provisional App. No. 62/342,270, filed May 27, 2016.

BACKGROUND

Technical Field

The present disclosure generally relates to the field of optical systems and methods. More particularly, and without limitation, the disclosed embodiments relate to systems and methods for tunable spectral filtering of an optical beam.

Many optical applications require optical filtering or wavelength selection of an optical beam to obtain higher signal-to-noise ratio or to resolve the spectral details of the optical signal for further analysis. In single point systems or line-scanning systems, optical filtering is commonly achieved using prisms or diffraction gratings. In two-dimensional (2-D) imaging systems, these optical elements are not suitable for filtering an optical beam carrying a 2-D image. This is because at least one spatial dimension is used for spreading out the spectrum of the optical beam. Some approaches that use a prism or a diffraction grating require acquisition of individual frames with one-dimensional spatial information along one axis and spectral information along the other. These frames are then used to build a 2-D image. However, such approaches are slow and do not allow for sharp edges in the filtered spectrum, and their spectral performance varies for different bandwidths.

In 2-D imaging systems, it is more desirable to have a uniform optical spectral transfer function across the field of view such that 2-D images having 2-D spatial information can be captured. For example, in fluorescence imaging or hyperspectral imaging, bandpass optical filtering is desirable to control and/or analyze the spectra of the excitation light and emission light. In such applications, prisms or diffraction gratings do not allow for substantially uniform transmission within a given passband across the field of view. Further, it is also desirable for a user to be able to tune the span and center wavelength of the spectrum of the filtered optical beam. This would allow the user to capture hyperspectral-imaging dataset with adjustable spectral bands and/or different spectral resolutions, for example. Currently, it is challenging to achieve such tunable filtering of an optical beam in a 2-D imaging system, especially when the divergence of the incident optical beam is high.

Some approaches try to achieve tunable optical filtering for 2-D imaging systems, but have their disadvantages and thus limited success. For example, a straightforward approach is to use a bank of bandpass filters, which are swapped to filter the optical beam into discrete spectral bands with excellent transmission (>90%) and very steep edges. However, this approach is limited by its high cost, low speed, and little flexibility. If the user would want to access any spectral band with any center wavelength, an infinite number of bandpass filters would be needed. Many commercial fluorescence microscopes employ this approach by using only a limited number of bandpass filters to capture images with a few discrete spectral bands. The bandwidths and center wavelengths of these spectral bands cannot be adjusted.

Some recent approaches use liquid crystal tunable filters (LCTF), acousto-optic tunable filters (AOTF), or linear variable tunable filters (LVTF) to achieve tunable optical filtering for 2-D imaging systems. However, these tunable filters also have their respective disadvantageous and limitations. For example, although LCTF offer reasonably fast center wavelength switching and large apertures suitable for 2-D imaging, LCTF are limited by their low transmission, poor band steepness, and fixed bandwidth. LCTF mostly transmit linearly polarized light with a particular polarization direction and their transmission for that polarization is often about 30% to about 50%. Additionally, their band steepness is not high and their ability to adjust the bandwidth is limited. AOTF offer wide tuning range and high tuning speed (fast wavelength switching). However, AOTF are also polarization sensitive, have poor band steepness, and lack adjustable bandwidth. LVTF offer high transmission, excellent band steepness, and adjustable bandwidth, and are polarization insensitive (transmission does not dependent polarization direction of the light). However, LVTF impart a chirp across the field of view due to the variation of their spectral properties across a none-zero width of an optical beam. Additionally, the tuning speed of LVTF is low due to the need to translate the LVTF mechanically.

Therefore, there is a need for methods and systems for tunable optical filtering of an optical beam suitable for 2-D imaging applications.

SUMMARY

The embodiments of the present disclosure provide systems and methods for achieving tunable optical filtering. Advantageously, the exemplary embodiments allow for flexible tuning of the bandwidths and center wavelengths of a desired number of passbands suitable for 2-D imaging systems.

According to an exemplary embodiment of the present disclosure, a system for filtering an input optical beam is described. The system includes a first beamsplitter, a first spectral slicing module, a second spectral slicing module, and a second beamsplitter. The first beamsplitter is configured to split the input optical beam into a first optical beam and a second optical beam. The first spectral slicing module has a first passband and is configured to filter the first optical beam. The second spectral slicing module has a second passband and is configured to filter the second optical beam. The second beamsplitter is configured to combine the first optical beam and the second optical beam into an output optical beam. The first and second spectral slicing modules may each comprise a longpass filter and a shortpass filter aligned along its optical axis, and the longpass filter and/or the shortpass filter are rotatable relative to the optical axis.

According to a further exemplary embodiment of the present disclosure, a method for filtering an input optical beam is described. The method includes the steps of splitting the input optical beam into a first optical beam and a second optical beam using a first beamsplitter; filtering the first optical beam by transmitting the first optical beam through a first spectral slicing module having a first passband; filtering the second optical beam by transmitting the second optical beam through a second spectral slicing module having a second passband; and combining the first and second optical beams into an output optical beam using a second beamsplitter. The first and second spectral slicing modules may each comprise a longpass filter and a shortpass filter aligned along its optical axis, and the longpass filter and/or the shortpass filter are rotatable relative to the optical axis.

According to a yet further exemplary embodiment of the present disclosure, a method for configuring an imaging system is described. The method includes the steps of splitting an input optical beam into a first optical beam and a second optical beam using a first beamsplitter; filtering the first optical beam by transmitting the first optical beam through a first spectral slicing module having a first passband; filtering the second optical beam by transmitting the second optical beam through a second spectral slicing module having a second passband; and combining the first and second optical beams into an output optical beam using a second beamsplitter. The first and second spectral slicing modules may each comprise a longpass filter and a shortpass filter aligned along its optical axis, and the longpass filter and/or the shortpass filter are rotatable relative to the optical axis.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Figure 1:
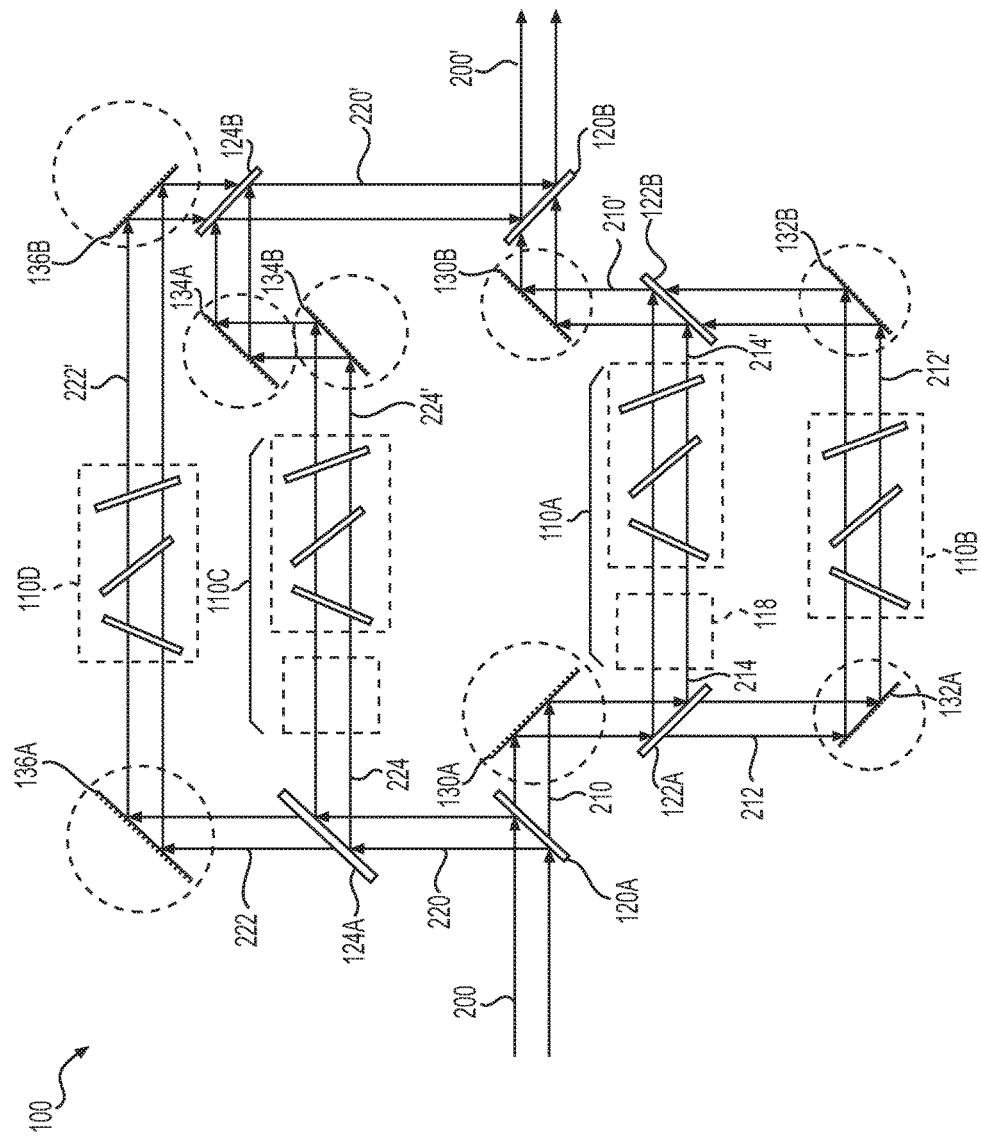
FIG. 1 is a schematic representation of an exemplary system for filtering an optical beam, according to embodiments of the present disclosure.

The disclosed embodiments relate to systems and methods for filtering an optical beam. Advantageously, the exemplary embodiments may selectively transmit one or more spectral bands with tunable bandwidths and/or center wavelengths, thereby allowing for obtaining a resultant optical beam with desired spectral bands and/or spectral resolutions. Embodiments of the present disclosure may be implemented in a spectrometer, e.g., an imaging spectrometer, a microscope, e.g., a fluorescence microscope, a confocal microscope, a transmission microscope, a reflectance microscope, etc., or a spectral imaging system, e.g., a hyperspectral imaging system. Alternatively, embodiments of the present disclosure may be implemented in a customized imaging system built using suitable optical elements.

According to an aspect of the present disclosure, an optical system is provided for filtering an input optical beam. The input optical beam may have a discrete spectrum or a continuous spectrum with a plurality of wavelengths. The input optical beam may be an excitation light beam for illuminating a sample or an emission light beam collected from a sample. The input optical beam may be filtered by the optical system to generate an output optical beam having selected spectral bands with desired bandwidths and/or center wavelengths.

According to an aspect of the present disclosure, the optical system may include one or more spectral slicing modules. Each spectral slicing module may have a passband that can be flexibly tuned to have a desired bandwidths and/or a desired center wavelength. In some embodiments, the optical system may be placed at a collimated space in an optical setup. In other embodiments, the optical system may collimate the input optical beam before the filtering and/or may focus the output optical beam after the filtering.

According to an aspect of the present disclosure, the optical system may split an input optical beam into at least two partial optical beams. For example, one or more beamsplitters may be used to split the input optical beam into a desired number of partial optical beams. At least one of the partial optical beams may be directed to transmit through a spectral slicing module. The spectral slicing module may filter the partial optical beam by transmitting wavelengths within its passband and reflecting wavelengths outside its passband. The optical system may then combine the partial optical beams, whether filtered or not, into an output optical beam using one or more beamsplitters and/or mirrors, for example.

In some embodiments, the partial optical beams having different spectral bands may be directed through a corresponding number of spectral slicing modules respectively. Each spectral slicing module may filter the partial optical beam transmitting through it to a desired spectral band. The optical system may then combine the filtered partial optical beams into an output optical beam using one or more beamsplitters and/or mirrors.

According to an aspect of the present disclosure, a beamsplitter for splitting the input optical beam may be a dichroic beamsplitter that selectively transmits and reflects light on the basis of wavelength. For example, an input optical beam incident on the dichroic beamsplitter may be spectrally split into two partial optical beams having two different spectral bands divided around a cut-off wavelength. One partial optical beam may transmit through the dichroic beamsplitter and the other may reflect off from the dichroic beamsplitter.

In some embodiments, the dichroic beamsplitter may have a passband (spectral region of high transmission/low reflectivity), a stopband (spectral region of low transmission/high reflectivity), and a transition region (the spectral region between the passband and stopband). The transition region may be defined as the region between two wavelengths, e.g., a first wavelength at about 90% and a second wavelength at about 10% peak transmission respectively. A cut-off wavelength at about 50% peak transmission may be at the center of the transition region.

According to an aspect of the present disclosure, a beamsplitter for combining two partial optical beams may allow the two partial optical beams to propagate along a common optical path after the combination. For example, a beamsplitter for combining the partial optical beams may be a dichroic beamsplitter that selectively transmits and reflects light on the basis of wavelength. One partial optical beam may transmit through the dichroic beamsplitter along its optical path and the other may reflect off from the dichroic beamsplitter to propagate along the same optical path.

In certain aspects, the beamsplitter for combining two partial optical beams into an output optical beam may have the same spectral characteristics as those of the beamsplitter for splitting the input optical beam into the two partial optical beams. For example, the two beamsplitters may be identical dichroic beamsplitters that reflect and transmit light based on the same cut-off wavelength. Advantageously, using identical dichroic beamsplitters for the splitting and combining allows for high transmission and high reflection of the two spectral bands of the two partial optical beams. This further allows for efficient direction and/or collection of the different partial optical beams split from the input optical beam to the combined output optical beam, thereby reducing loss of light.

According to an aspect of the present disclosure, the spectral slicing modules may each operate as a bandpass filter with a tunable passband. The bandwidth and/or center wavelength of the passband of each spectral slicing module may be independently adjustable to desired values. In some embodiments, each spectral slicing module may include a longpass filter and a shortpass filter aligned along its optical axis. The longpass filter and shortpass filter are independently rotatable relative to the optical axis. Rotating either of the filters may change the angle of incidence (AOI) of the partial optical beam upon the filter and thus shift the absorption or reflection edge, e.g., cut-off wavelength. For example, increasing the AOI from normal incidence to higher angles may shift the spectral transmission of the longpass filter and/or shortpass filter towards shorter wavelengths. Thus, the passband of each spectral slicing module (e.g., the bandwidth and/or center wavelength) may be tuned by rotating at least one of its longpass and/or shortpass filters relative to the optical axis.

Advantageously, the passband of each spectral slicing module varies as a function of the AOI upon the longpass and/or shortpass filters without exhibiting substantial change in the shape of the spectrum, the percentage transmission, and/or the out-of-band rejection. Additionally, the bandwidth and/or center wavelength of the passband of each spectral slicing module may be continuously tuned over an entire possible passband by changing the AOI of the partial optical beam upon the filters. Further, by using a series of spectral slicing modules with different passbands, the spectrum of the input optical beam may be selectively filtered to have spectral bands with desired bandwidths and center wavelengths.

In certain aspects, the spectral slicing modules may have a series of passbands spectrally shifted from one another with overlapping regions between two adjacent passbands. For example, two different spectral slicing modules may have two different passbands for filtering two partial optical beams. The two passbands may have an overlapping region, and a first passband may span across wavelengths generally longer than the second passband. In such instances, the transition region of the dichroic beamsplitter for splitting an input optical beam into the two partial optical beams may fall within this overlapping region. Advantageously, such characteristics of the dichroic beamsplitter and the spectral slicing modules reduce potential artifacts that may result from the spectral splitting of the input optical beam and separate filtering of the partial optical beams.

In certain aspects, at least one of the spectral slicing modules may further include a blocking filter that additionally blocks wavelengths outside of the passband of the spectral slicing module. For example, the blocking filter may be a bandpass filter that substantially blocks or rejects wavelengths beyond the passband formed by the longpass and shortpass filters, thereby reducing or eliminating spectral irregularities beyond the passband.

In certain aspects, the optical system may further include one or more mirrors configured to direct the propagation of the input optical beam, the partial optical beams split from the input optical beam, and/or the output optical beam. In some embodiments, a pair of mirrors may be configured to align a partial optical beam along the optical axis of a spectral slicing module. For example, a first mirror may receive the partial optical beam and direct it through the components of the spectral slicing module, e.g., longpass and shortpass filters. A second mirror may receive the filtered partial optical beam, and may further direct it towards a beamsplitter to be combined with another partial optical beam. The two mirrors may be independently and suitably adjusted to align the propagation of the partial optical beam along the optical axis of the spectral slicing module. Advantageously, aligning the different partial optical beams along the optical axes of the spectral slicing modules respectively may eventually allow the partial optical beams to propagate along the same direction or the same optical path after they are combined.

In certain aspects, a spectral slicing module may further include a compensation filter that realigns the partial optical beam when it is laterally deviated from the optical axis after transmitting through the longpass and/or shortpass filters. For example, a partial optical beam transmitting through the longpass and/or shortpass filters at a non-normal AOI may have a lateral displacement from the optical axis of the spectral slicing module. The compensation filter may correct the lateral displacement and realign the input optical axis and the output optical axis of the spectral slicing module.

In some embodiments, the output optical beam may propagate along the same direction as the input optical beam does. For example, the input optical beam and the output optical beam of the system may remain collinear, thereby advantageously maintaining the direction of the overall optical axis of the optical system.

In certain aspects, a spectral slicing module may further include an optical spatial compensator that adds optical path length to the partial optical beam transmitting through it. For example, a first spectral slicing module may have an optical path length (OPL) longer than a second spectral slicing module. Therefore, an optical path difference (OPD) may exist between a first partial optical beam traveling through the first spectral slicing module and a second partial optical beam traveling through the second spectral slicing module. In such instances, the second spectral slicing module may include an optical spatial compensator, e.g., a glass plate, that adds OPL traveled by the second partial optical beam. Advantageously, the addition of the optical spatial compensator reduces the OPD between the two partial optical beams when they are combined in the output optical beam. This may further reduce or eliminate undesirable optical effects, e.g., interference, that may result from a OPD between the two partial optical beams.

As described herein, the optical beam entering the optical system to be filtered may be referred to as an input optical beam, and the filtered optical beam exiting the optical system may be referred to as an output optical beam. In some embodiments, the output optical beam may be further dispersed, modulated, filtered, processed, and/or detected by a one-dimensional or two-dimensional array of photodetector or sensor of an imaging device.

Reference will now be made in detail to embodiments and aspects of the present disclosure, examples of which are illustrated in the accompanying drawings.

FIG. 1 is a schematic representation of an exemplary system 100 for filtering an optical beam. For example, system 100 may be implemented in an optical setup for generating an output optical beam 200' with a desired spectrum from an input optical beam 200. As described herein, input optical beam 200 refers to the optical beam entering and/or transmitting through system 100 and output optical beam 200' refers to the filtered optical beam exiting system 100. Input optical beam 200 and output optical beam 200' are referenced separately for describing the transmission and filtering of the optical beam by system 100. In some embodiments, output optical beam 200' may be further dispersed, filtered, modulated, and/or acquired to obtain an optical signal with a desired spectrum and/or spectral resolution.

As shown in FIG. 1, system 100 may include one or more spectral slicing modules, e.g., spectral slicing modules 110A, 110B, 110C, and 110D; a first set of beamsplitters, e.g., beamsplitters 120A, 122A, and 124A; and a second set of beamsplitters, e.g., beamsplitters 120B, 122B, and 124B. The first set of beamsplitters may be used to split an optical beam into separate partial optical beams with different spectral bands. For example, beamsplitter 120A may be a dichroic beamsplitter that splits input optical beam 200 at a first cut-off wavelength, generating two partial optical beams 210 and 220 with two different spectral bands. Similarly, beamsplitter 122A further splits optical beam 210 into two partial optical beams 212 and 214 at a second cut-off wavelength, and beamsplitter 124A further splits optical beam 220 into two partial optical beams 222 and 224 at a third cut-off wavelength. Therefore, the partial optical beams 212, 214, 222, or 224 split from input optical beam 200 may each have a different spectral band.

As described herein, splitting input optical beam 200 into four partial optical beams 212, 214, 222, and 224 as shown in FIG. 1 is used only by way of example. It is also possible to split input optical beam 200 into a smaller or greater number of partial optical beams as desired. In that case, it would merely be necessary to provide a corresponding quantity of beamsplitters. For example, beamsplitter 124A may be replaced by a mirror such that optical beam 220 is not further split into additional partial optical beams. Alternatively, additional beamsplitters may be added to further split optical beams 212 and/or 222. It is also possible to block one or more partial optical beams so that the spectral bands corresponding to those partial optical beams are substantially removed from the spectrum of output optical beam 200'.

As described above, when a beamsplitter is a dichroic beamsplitter, two partial optical beams split by the beamslitter from an input optical beam would have different spectral bands. In other embodiments, a beamsplitter other than a dichroic beamsplitter may be used in system 100. In such instances, two partial optical beams split by the beamsplitter may have the same spectrum, and may be further separately filtered by transmitting through different spectral slicing modules.

In some embodiments, at least one of the partial optical beams 212, 214, 222, or 224 may be directed through a spectral slicing module. The spectral slicing module then filters the partial optical beam transmitting through it to a desired spectral band having a desired bandwidth and/or center wavelength.

For example, as shown in FIG. 1, partial optical beams 212, 214, 222, or 224 may be respectively directed through a different spectral slicing module. The spectral slicing modules 110A, 110B, 110C, and 110D, may each operate as a tunable bandpass filter with an adjustable bandwidth and an adjustable center wavelength. Therefore, the spectral slicing modules may each filter the partial optical beam transmitting through it and generate corresponding filtered partial optical beams 212', 214', 222', or 224', with desired spectral bands.

As described herein, the four exemplary spectral slicing modules 110A, 110B, 110C, and 110D, for respectively filtering the four partial optical beams are described only by way of example. It is also possible to use a smaller or greater number of spectral slicing modules, and a selected number of partial optical beams may be selected and directed through the spectral slicing modules. In such instances, a corresponding number of beamsplitters and/or mirrors may be used in system 100.

The second set of beamsplitters may be used to combine the filtered partial optical beams 212', 214', 222', or 224' into the output optical beam 200'. For example, beamsplitter 122B may be a dichroic beamsplitter that transmits optical beam 212' and reflects optical beam 214', thereby generating a combined optical beam 210' with a spectrum combining the spectral bands of optical beams 212' and 214'. Similarly, beamsplitter 124B may be a dichroic beamsplitter that transmits optical beam 222' and reflects optical beam 224', thereby generating a combined optical beam 220' with a spectrum combining the spectral bands of optical beams 222' and 224'. Beamsplitter 120B may also be a dichroic beamsplitter that further transmits the combined optical beam 210' and reflects the combined optical beam 220', thereby generating output optical beam 200'. Therefore, output optical beam 200' of system 100 would have a spectrum combining the spectral bands of optical beams 212', 214', 222', and 224'.

In some embodiments, the second set of beamslitters may have spectral characteristics matching those of the first set of beamsplitters to reduce the loss of light. For example, beamsplitters 122A and 122B may be similar or identical dichroic beamplitters having the same cut-off wavelength. Similarly, beamsplitters 124A and 124B may be similar or identical dichroic beamplitters having the same cut-off wavelength, and beamsplitters 120A and 120B may be similar or identical dichroic beamplitters having the same cut-off wavelength. This matching configuration of the first and second sets of beamsplitters may allow for highly efficient transmission and reflection of the partial optical beams by reducing the mismatching of the cut-off wavelengths of these beamsplitters. Advantageously, this may further increase the efficiency of directing the partial optical beams split from input optical beam 200 to the combined output optical beam 200', thereby reducing loss of light In some embodiments, system 100 may further include one or more mirrors for independently aligning the partial optical beams transmitting through the corresponding spectral slicing modules. The mirrors may be used in pairs for performing the alignment. For example, as shown in FIG. 1, a first pair of mirrors 130A and 130B may be adjusted to align the direction of optical beam 214 along the optical axis of spectral slicing module 110A. Similarly, a second pair of mirrors 132A and 132B may be adjusted to align the direction of optical beam 212 along the optical axis of spectral slicing module 110B; a third pair of mirrors 134A and 134B may be adjusted to align the direction of optical beam 224 along the optical axis of the spectral slicing module 110C; and a fourth pair of mirrors 136A and 136B may be adjusted to align the direction of optical beam 222 along the optical axis of the spectral slicing module 110D.

In some cases, a pair of mirrors for aligning a partial optical beam, e.g., mirrors 132A and 132B, may be separately placed at two ends of the corresponding spectral slicing module along its optical axis. In other cases, a pair of mirrors for aligning a partial optical beam, e.g., mirrors 134A and 134B, may be placed at the same end of the corresponding spectral slicing module along its optical axis. The mirrors of system 100 may be independently tilted and/or rotated manually or using motorized devices. For example, the mirrors may be adjusted using stepper, servo, or DC motorized rotational stages. Alternatively, pairs of mirrors may be replaced with pairs of galvanometer scanners or galvo mirrors.

Advantageously, independent alignment of the partial optical beams along the optical axes of the spectral slicing modules allows the filtered partial optical beams to propagate along the same direction or the same optical path after they are combined. For example, as shown in FIG. 1, optical beams 212' and 214' would propagate along the same direction after being combined into optical beam 210' by beamsplitter 122B. Similarly, optical beams 222' and 224' would propagate along the same direction after being combined into optical beam 220' by beamsplitter 124B, and optical beams 210' and 220' would then propagate along the same direction after being further combined into output optical beam 200' by beamsplitter 120B.

Functions and the working principles of the spectral slicing modules of system 100 are described in detail below.

Figure 2:
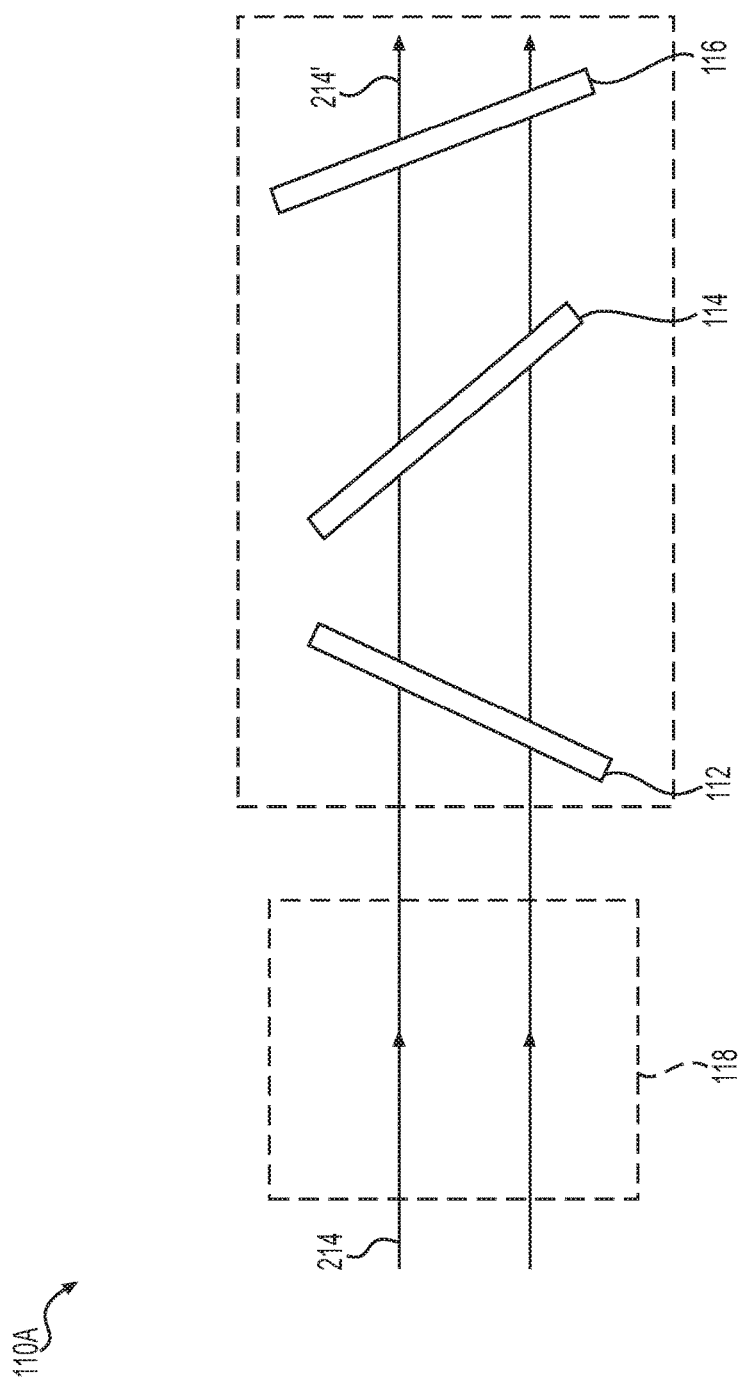
FIG. 2 is a schematic representation of an exemplary spectral slicing module for filtering an optical beam, according to embodiments of the present disclosure.

FIG. 2 is a schematic representation of an exemplary spectral slicing module for filtering an optical beam. As described herein, descriptions of the features below in references to spectral slicing module 110A are equally applicable to other spectral slicing modules of system 100, e.g., spectral slicing modules 110B, 110C, and 110D.

As shown in FIG. 2, spectral slicing module 110A may include a longpass filter 112 and a shortpass filter 114 aligned along its optical axis. Longpass filter 112 and shortpass filter 114 may in combination form a bandpass filter with a passband delineated by their edge wavelengths or cut-off wavelengths (the cut-off wavelength of longpass filter 112 is smaller than that of shortpass filter 114). At least one of the longpass filter 112 and shortpass filter 114 is rotatable relative to the optical axis. For example, longpass filter 112 and shortpass filter 114 may be independently rotatable to be at an angle relative to the optical axis.

In some embodiments, longpass filter 112 and shortpass filter 114 may be thin-film angle-tuning filters. Rotating longpass filter 112 may adjust the angle of incidence (AOI) of optical beam 214 upon its surface. The cut-off wavelength of longpass filter 112 may vary as a function of the AOI. Similarly, rotating shortpass filter 114 may adjust the AOI of optical beam 214 upon its surface and the cut-off wavelength of shortpass filter 114 may vary as a function of the AOI.

For example, rotating longpass filter 112 to change the AOI of optical beam 214 upon its surface from normal incidence to higher angles may shift the cut-off wavelength of longpass filter 112 towards shorter wavelengths. Alternatively, rotating longpass filter 112 to change the AOI from higher angles to normal incidence may shift the cut-off wavelength of longpass filter 112 towards longer wavelengths. Similarly, rotating shortpass filter 114 to change the AOI of optical beam 214 upon its surface from normal incidence to higher angles may shift the cut-off wavelength of shortpass filter 114 towards shorter wavelengths. Rotating shortpass filter 114 to change the AOI from higher angles to normal incidence may shift the cut-off wavelength of shortpass filter 114 towards longer wavelengths.

Accordingly, tuning the AOI of optical beam 214 upon longpass filter 112 and/or upon shortpass filter 114 varies the cut-off wavelengths of the passband of spectral slicing module 110A, thereby allowing for adjustment of the bandwidth and/or center wavelength of the passband. The AOI of optical beam 214 upon longpass filter 112 and/or shortpass filter 114 may be independently and continuously tuned across a given range of adjustment, e.g., from about −10° to about 60°. This may advantageously allow the passband of spectral slicing module 110A to be continuously tuned to have any desired bandwidth and/or center wavelength across a given spectral range that could be provided by the filters.

As described herein, the order of optical beam 214 transmitting through longpass filter 112 and shortpass filter 114 would not affect the tunable bandpass filtering of optical beam 214 by spectral slicing module 110A. This also applies to the other spectral slicing modules for filtering other partial optical beams in system 100.

Comparing to a single tunable bandpass filter whose predetermined passband may be shifted by tuning the AOI of the optical beam on the filter, spectral slicing module 110A advantageously allows for flexible adjustment of the bandwidth and/or the center wavelength of its passband by independently tuning the two cut-off wavelengths of the passband. Additionally, comparing to other tunable optical filters, such as liquid crystal tunable filters (LCTF), acousto-optic tunable filters (AOTF), or linear variable tunable filters (LVTF), spectral slicing module 110A allow for high transmission, sharp cut-off edges, and polarization insensitivity provided by the longpass and shortpass filters.

In some situations, when optical beam 214 transmits through longpass filter 112 and/or shortpass filter 114 at non-normal angles, filtered optical beam 214' may laterally deviate from the optical axis of spectral slicing module 110A. In such situations, as shown in FIG. 2, spectral slicing module 110A may further include a compensation filter 116 aligned along its optical axis after longpass filter 112 and shortpass filter 114. Compensation filter 116 may be rotated to be at a suitable angle relative to the optical axis to generate an opposite lateral deviation to correct the lateral displacement of optical beam 214'. In some embodiments, compensation filter 116 may be adjusted to be at an angle relative to the optical axis ranging from about 0° to about 30°.

In some embodiments, compensation filter 116 may be adjusted together with mirrors to align the filtered optical beam 214' along the optical axis of spectral slicing module 110A. For example, mirrors 130A and 130B and compensation filter 116 may be independently adjusted to allow optical beam 214' to propagate along the optical axis of spectral slicing module 110A. Similar alignment may be performed for other optical beams, e.g. optical beams 212', 222', and 224'. Additionally, as shown in FIG. 1, such independent alignment of the filtered partial optical beams may further allow them to propagate along the same optical path after they are combined into one optical beam (e.g., optical beams 210', 220', and 200').

In some embodiments, longpass filter 112, shortpass filter 114, and/or compensation filter 116 may be independently rotated using motorized rotational devices. For example, these filters may be adjusted using stepper, servo, or DC motorized rotational stages. Alternatively, these filters may be rotated using galvanometer scanners.

In some situations, separate optical beams, e.g., optical beams 212 and 214, may propagate through different optical path lengths (OPL). For example, as shown in FIG. 1, due to the geometry of system 100, optical beam 212' may propagate through an OPL longer than that of optical beam 214' when they are combined at beamsplitter 122B. The optical path length difference (OPD) between optical beams 212' and 214' may result in a phase shift between them when they are combined. In some instances, this phase shift may generate undesirable optical effects, e.g., interference. Therefore, in some embodiments, spectral slicing module 110A may further include an optical spatial compensator 118.

Optical spatial compensator 118 may add OPL to the optical beam transmitting through it. Optical spatial compensator 118 may be a glass plate with a selected thickness and refractive index. For example, as shown in FIG. 1, optical spatial compensator 118 may add to the OPL traveled by optical beam 214' to be the same as that traveled by optical beam 212'. Advantageously, the addition of optical spatial compensator 118 may allow two partial optical beams transmitting along two different paths in system 100 to propagate through the same amount of OPL upon being combined into one optical beam, thereby reducing or eliminating undesirable optical effects.

In some embodiments, spectral slicing module 110A may further include a blocking filter (not shown) that further blocks or rejects wavelengths outside of a desired passband of the spectral slicing module 110A. For example, the blocking filter may be a bandpass filter that substantially blocks or rejects wavelengths beyond the passband formed by longpass filter 112 and shortpass filter 114. This advantageously allows for reducing or eliminating potential non-ideal spectral irregularities beyond the passband. Additionally or alternatively, spectral slicing module 110A may further include another compensation filter (not shown) that compensates for astigmatism to improve the sharpness of the filtered optical beam 214'. This may further improve the sharpness of output optical beam 200'.

Figure 3A:
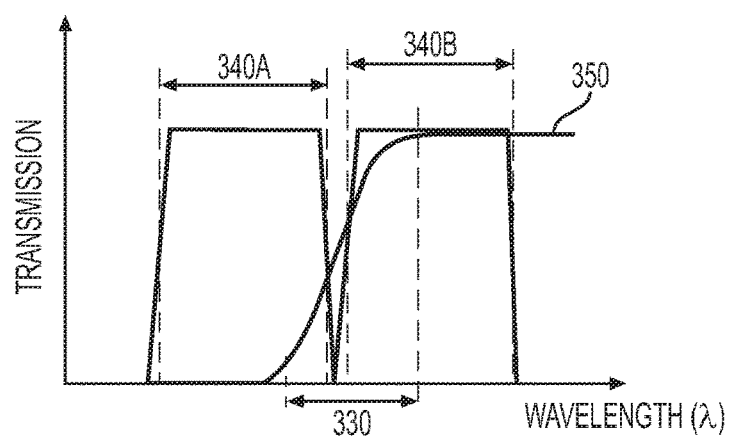
FIG. 3A is a graphical illustration for two exemplary passbands of two spectral slicing modules, according to embodiments of the present disclosure.
Figure 3B:
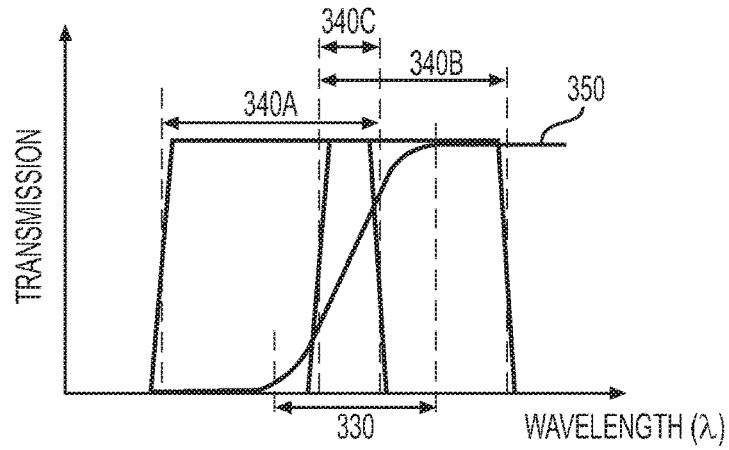
FIG. 3B is a graphical illustration for another two exemplary passbands of two spectral slicing modules, according to embodiments of the present disclosure.
Figure 3C:
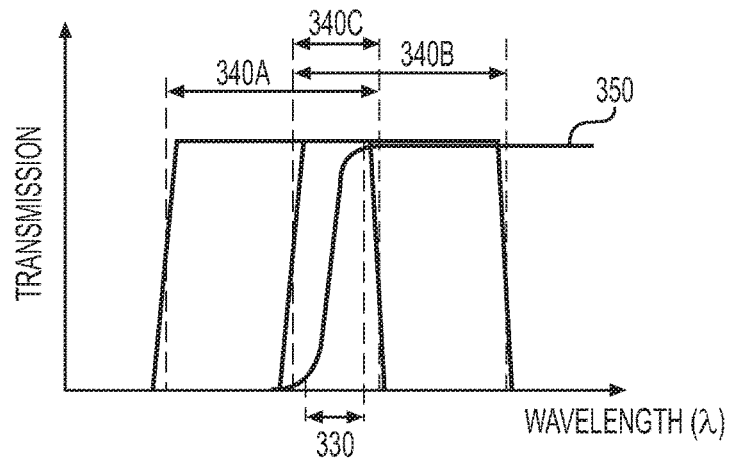
FIG. 3C is a graphical illustration for another two exemplary passbands of two spectral slicing modules, according to embodiments of the present disclosure.

As described above, the spectral slicing modules may have a series of passbands spectrally shifted from one another with overlapping regions between two adjacent passbands. In such instances, the transition region of the dichroic beamsplitter for splitting an input optical beam into the two partial optical beams is selected to be within the overlapping region to reduce potential artifacts from the splitting and separate filtering of the partial optical beams. FIGS. 3A-3C graphically illustrate the advantage of such characteristics of the dichroic beamsplitter and the spectral slicing modules for reducing loss of light. FIGS. 3A-3C show two exemplary passbands 340A and 340B of spectral slicing modules 110A and 110B with amount of transmission (e.g., percentage transmission) along the vertical axis and wavelength along the horizontal axis. Additionally, FIGS. 3A-3C show an exemplary transmission spectrum 350 of beamsplitter 122A having a transition region 330.

As shown in FIG. 1 and FIG. 3A, passbands 340A and 340B do not overlap. In such instances, wavelengths of optical beam 210 at the center of transition region 330 partially transmit through and reflect from beamsplitter 122A. However, because passbands 340A and 340B do not overlap, and may have gap regions due to the slopes of their edges, at least a portion of optical beam 210 at these wavelengths at the center of transition region 330 cannot pass through either passband 340A or 340B. This results in losing a portion of optical beam 210 at these wavelengths. Further, wavelengths of optical beam 210 at the two edges of transition region 330 may be subjected to additional loss. For example, some wavelengths of optical beam 210 in transition region 330 may substantially transmit through beamsplitter 122A and then through passband 340B of spectral slicing module 110B. But these wavelengths of optical beam 210 are also partially reflected from beamsplitter 122A and directed towards spectral slicing module 110A. However, these wavelengths do not fall in passband 340A of spectral slicing module 110A, thereby resulting in losing a portion of optical beam 210 at these wavelengths.

As shown in FIG. 1 and FIG. 3B, passbands 340A and 340B have an overlapping region 340C narrower than transition region 330 of beamsplitter 122A. In such instances, the wavelengths of optical beam 210 at the center of transition region 330 would transmit through passbands 340A and 340B, thereby reducing loss of optical beam 210. However, wavelengths of optical beam 210 at the two edges of transition region 330 that are outside of overlapping region 340C may still be subjected to additional loss. For example, some wavelengths of optical beam 210 outside overlapping region 340 but inside transition region 330 may substantially transmit through beamsplitter 122A and then through passband 340B of spectral slicing module 110B. But these wavelengths of optical beam 210 are also partially reflected from beamsplitter 122A and directed towards spectral slicing module 110A. However, these wavelengths do not fall in passband 340A of spectral slicing module 110A. This again results in losing a portion of optical beam 210 at these wavelengths.

As shown in FIG. 1 and FIG. 3C, according to embodiments of the present disclosure, passbands 340A and 340B have an overlapping region 340C equal to or wider than transition region 330 of beamsplitter 122A. In such instances, wavelengths of optical beam 210 in transition region 330 would fall in both passbands 340A and 340B. This allows for portions of optical beam 210, whether reflecting from or transmitting through beamsplitter 122A, to transmit through passband 340A of spectral slicing module 110A and/or passband 340B of spectral slicing module 110B, thereby advantageously reducing or eliminating of the loss of optical beam 210.

As described herein, the adjustment of the mirrors and angle-tuning of the filters of system 100 may be controlled by a controller (not shown). The controller may have a processor, a non-transitory memory, and a computer-readable medium that stores instructions or operational steps. The memory may store a plurality of coefficients of the filters, such as AOI and cut-off wavelengths, and parameters of the mirrors, e.g., angles relative to the optical axis along one or two spatial dimensions. The instructions or steps, when executed by the processor, may adjust the AOI of the optical beams upon the filters to suitable angles based on the desired passbands of the spectral slicing modules. Additionally, the instructions or steps, when executed by the processor, may further operate motorized rotational stages or galvanometer scanners to adjust the mirrors and/or compensation filters to align the output partial optical beams along the spectral slicing modules such that they would propagate along the same optical path after being combined.

Examples for filtering input optical beam 200 by system 100 to generate output optical beam 200' with desired spectral bands are further described below in reference to their spectra. As described above, an input optical beam 200 may be split into a plurality of partial optical beams having different spectral bands. The spectral bands of the partial optical beams may be selectively and independently filtered to desired spectral ranges by the corresponding spectral slicing modules. When the partial optical beams are combined into output optical beam 200', the spectral bands of the partial optical beams are then combined as the spectrum of output optical beam 200'.

Figure 4:
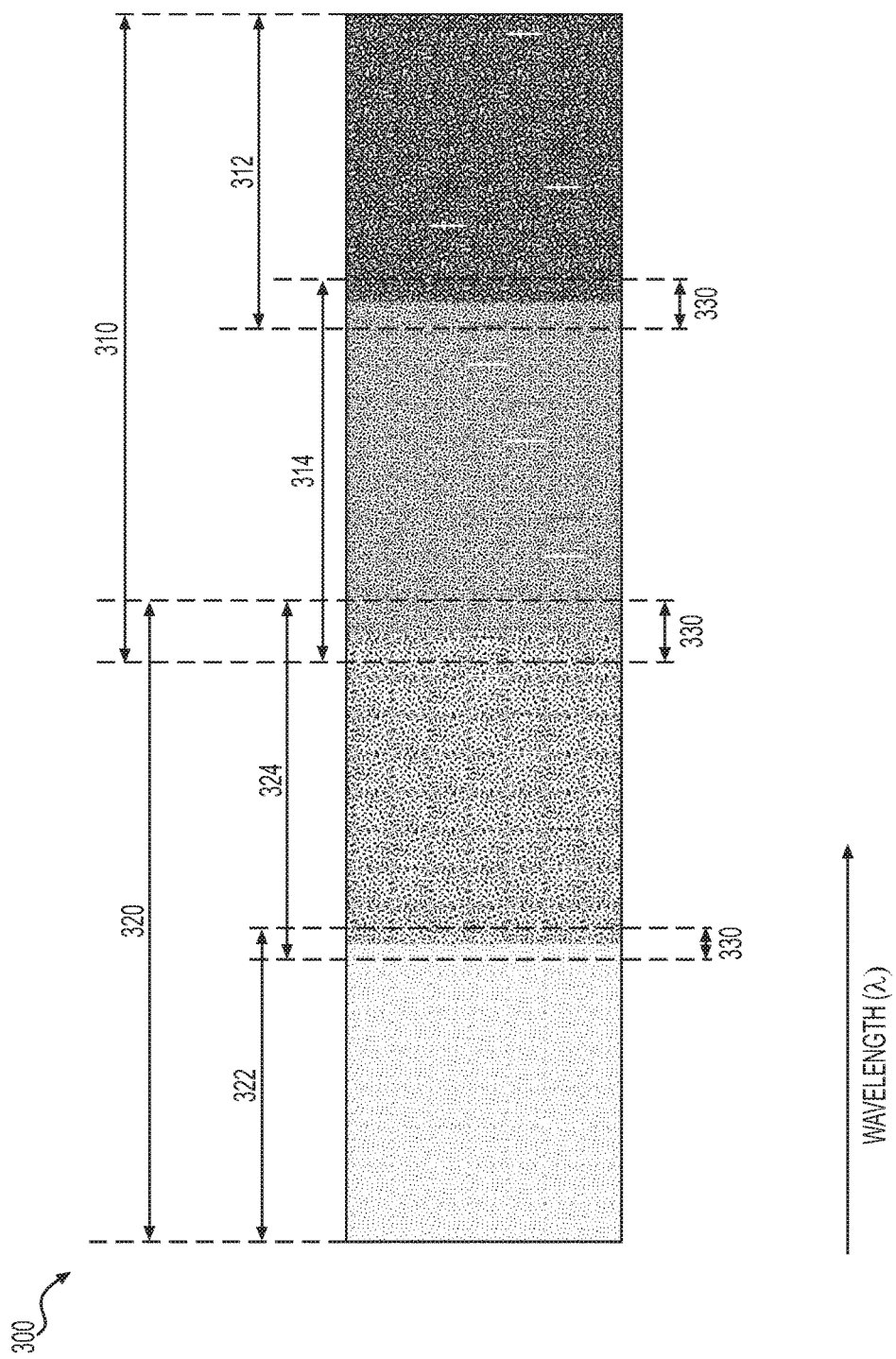
FIG. 4 is a graphical illustration for an exemplary spectrum of an input optical beam entering the exemplary system of FIG. 1, according to embodiments of the present disclosure.
Figure 5:
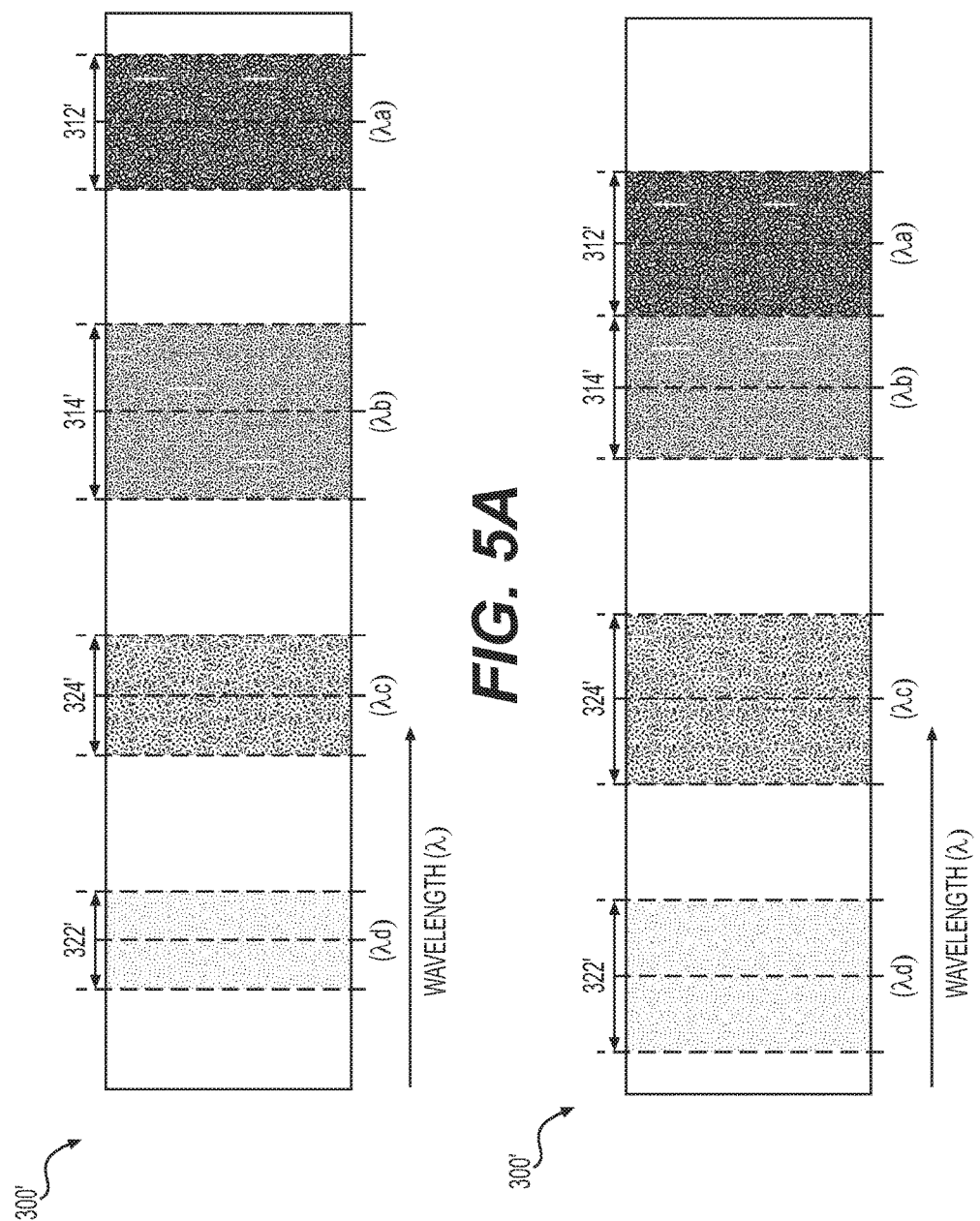
FIG. 5A is a graphical illustration for an exemplary spectrum of an output optical beam exiting the exemplary system of FIG. 1, according to embodiments of the present disclosure.
FIG. 5B is a graphical illustration for another exemplary spectrum of an output optical beam exiting the exemplary system of FIG. 1, according to embodiments of the present disclosure.

FIG. 4 is a graphical illustration for an exemplary spectrum 300 of input optical beam 200. FIGS. 5A and 5B are graphical illustrations for examples of the spectrum 300' of output optical beam 200'.

As shown in FIG. 4, spectrum 300 of input optical beam 200 may be split into four spectral bands 312, 314, 322, and 324, corresponding to the four partial optical beams 212, 214, 222, and 224. For example, spectrum 300 of input optical beam 200 may first be split into spectra 310 and 320, corresponding to optical beams 210 and 220. Spectrum 310 of optical beam 210 may then be further split into spectral bands 312 and 314, corresponding to optical beams 212 and 214. Similarly, spectrum 320 of optical beam 220 may then be further split into spectral bands 322 and 324, corresponding to optical beams 222 and 224. In some embodiments, as shown in FIG. 4, adjacent spectral bands may have overlapping bands due to the transition regions 330 of the beamsplitters.

As shown in FIGS. 5A and 5B, spectral bands 312, 314, 322, and 324 may be filtered by the corresponding spectral slicing modules to desired spectral bands 312', 314', 322', and 324', corresponding to the filtered optical beams 212', 214', 222', and 224'. Spectrum 300' of output optical beam 200' is the combination of the filtered spectral bands.

In one example, as shown in FIG. 5A, spectral band 312 of optical beam 212 may be filtered to a narrower spectrum 312' with a center wavelength $\lambda_a$. Additionally or alternatively, as shown in FIG. 5B, spectral slicing module 110A may be adjusted to tune the center wavelength $\lambda_a$ of spectral band 312' towards shorter wavelengths as desired. Spectral slicing module 110A may also be adjusted to tune the center wavelength $\lambda_a$ of spectral band 312' towards longer wavelengths as needed (not shown).

In another example, as shown in FIG. 5A, spectral band 314 of optical beam 214 may be filtered to a desired spectral band 314' with a center wavelength $\lambda_b$. Additionally or alternatively, as shown in FIG. 5B, spectral slicing module 110B may be adjusted to reduce the bandwidth of spectral band 314' and to shift the center wavelength $\lambda_b$ of spectral band 314' towards longer wavelengths as desired.

As shown in FIG. 5B, spectral band 312' of filtered optical beams 212' and spectral band 314' of filtered optical beams 214' can be substantially continuous, maintaining the continuity of spectra bands 312 and 314 of input optical beam 200 without substantial loss or no loss of light. This may be advantageously achieved by selectively using beamsplitter 122A with a transition region 330 equal to or narrower than that of overlapping region 340C of the passbands of spectral slicing modules 110A and 110B as described above.

In another example, as shown in FIG. 5A, spectral band 324 of optical beam 224 may be filtered to a desired spectral band 324' with a center wavelength $\lambda_c$. Additionally or alternatively, as shown in FIG. 5B, spectral slicing module 110C may be adjusted to increase the bandwidth of spectral band 324'. Spectral slicing module 110C may also be adjusted to shift the center wavelength $\lambda_c$ of spectral band 324' towards longer or shorter values (not shown).

In yet another example, as shown in FIG. 5A, spectral band 322 of optical beam 222 may be filtered to a desired spectral band 322' with a center wavelength $\lambda_d$. Additionally or alternatively, as shown in FIG. 5B, spectral slicing module 110D may be adjusted to increase the bandwidth of spectral band 322' and tune the center wavelength $\lambda_d$ towards shorter wavelengths as needed. Alternatively, spectral slicing module 110D may be adjusted to reduce the bandwidth of spectral band 322', and/or tune the center wavelength $\lambda_d$ towards shorter or longer wavelengths as needed (not shown).

As described herein, FIGS. 5A and 5B only provide exemplary tuning of the spectral filtering that can be provided by the spectral slicing modules of system 100. As described above, any of the spectral slicing modules may be adjusted to filter a partial optical beam to have any desired spectral band and center wavelength in a given spectral range. As describe herein, this given spectral range may be determined by the tunable ranges of cut-off wavelengths of the longpass and shortpass filters of each spectral slicing module.

Figure 6:
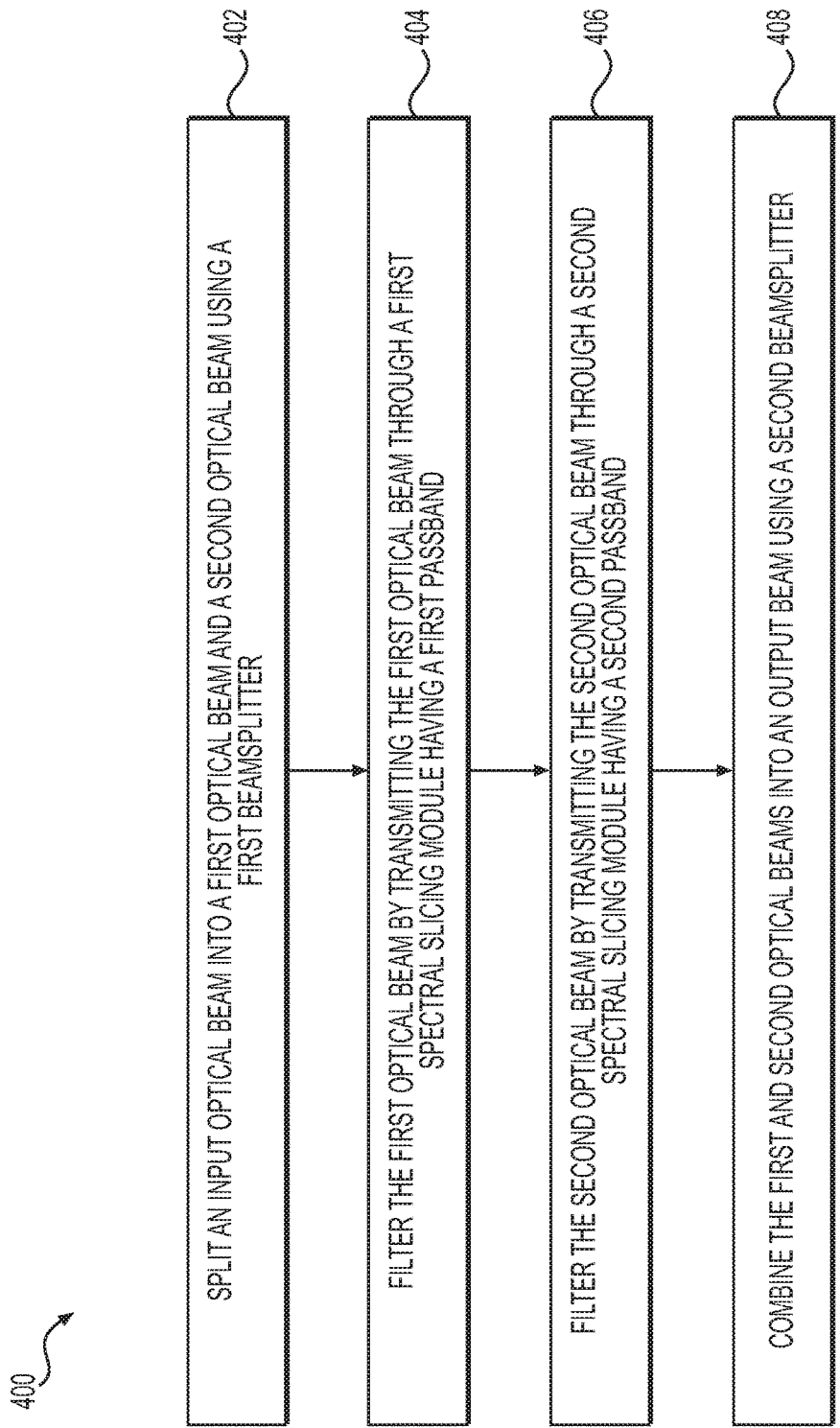
FIG. 6 is a flowchart of an exemplary method for filtering an optical beam, according to embodiments of the present disclosure.

System 100 as described herein may be utilized in a variety of methods and devices for filtering an optical beam. FIG. 6 is a flowchart of an exemplary method 400 for filtering of an optical beam. Method 400 uses system 100 and features of the embodiments of system 100 described above in reference to FIGS. 1-5.

At step 402, an input optical beam (e.g., optical beam 210) is split into a first optical beam (e.g., optical beam 214) and a second optical beam (e.g., optical beam 212) using a first beamsplitter (e.g., beamsplitter 122A). At step 404, the first optical beam is filtered by transmitting the first optical beam through a first spectral slicing module (e.g., spectral slicing module 110A) having a first passband (e.g., passband 340A). At step 406, the second optical beam (e.g., optical beam 214) is filtered by transmitting the second optical beam through a second spectral slicing module (e.g., spectral slicing module 120A) having a second passband (e.g., passband 340B). At step 408, the first optical beam may be combined with the second optical beam into an output optical beam (e.g., optical beam 210') using a second beamsplitter (e.g., beamsplitter 122B).

As described herein, an input optical beam may be split into a desired number of partial optical beams with different spectral bands using a suitable quantity of beamsplitters. The above-described steps may be performed for a plurality of times based on the number of spectral bands desired to be split and filtered of an input optical beam.

Various embodiments of method 400 may include one or more of the following features or steps. For example, method 400 may further include tuning a bandwidth and/or a center wavelength of the passband of at least one of the spectral splicing modules by varying the AOI of the partial optical beam upon its longpass filter 112 and/or the shortpass filter 114. In some embodiments, method 400 may further include directing the propagation of the first and/or second optical beams using one or more mirrors, e.g., pairs of mirrors. Method 400 may further include realigning the first and/or second optical beams laterally deviated from the optical axis after transmitting through the longpass and/or shortpass filters using one or more rotatable mirrors and/or compensation filters.

In some embodiments, method 400 may further include directing the first and second optical beams to propagate along the same direction or optical path after they are combined. Additionally, method 400 may further include directing the combined output optical beam to be collinear with the input optical beam.

In some embodiments, method 400 may further include additionally blocking the wavelengths outside of the passband of at least one of the spectral splicing modules using a blocking filter. Method 400 may further include adding optical path length to the first and/or second optical beams using at least one optical spatial compensator.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An optical system for filtering an input optical beam, comprising:
    a first beamsplitter configured to split the input optical beam into a first optical beam and a second optical beam, wherein the first beamsplitter is a dichroic beamsplitter that substantially transmits the first optical beam and substantially reflects the second optical beam;
    a first spectral slicing module having a first passband and configured to filter the first optical beam, wherein the first spectral slicing module comprises a first longpass filter and a first shortpass filter aligned along a first optical axis, wherein at least one of the first longpass filter or the first shortpass filter is rotatable relative to the first optical axis;
    a second spectral slicing module having a second passband and configured to filter the second optical beam, wherein the second spectral slicing module comprises a second longpass filter and a second shortpass filter aligned along a second optical axis, wherein at least one of the second longpass filter or the second shortpass filter is rotatable relative to the second optical axis, wherein the first and second passbands both include a first range of wavelengths, wherein the first beamsplitter has a transition region that spans a second range of wavelengths, and wherein the second range of wavelengths is narrower than the first range of wavelengths; and
    a second beamsplitter configured to combine the first optical beam and the second optical beam into an output optical beam.

2. The system of claim 1, wherein the first passband has at least one of a bandwidth or a center wavelength that varies with the rotation of the at least one of the first longpass filter or the first shortpass filter.

3. The system of claim 1, wherein at least one of the first longpass filter or the first shortpass filter is rotatable relative to the first optical axis by an angle ranging from −10° to 60°.

4. The system of claim 1, wherein the first spectral slicing module further comprises a blocking filter that blocks wavelengths of the first optical beam outside the first passband.

5. The system of claim 1, wherein the second beamsplitter is a dichroic beamsplitter.

6. The system of claim 1, further comprising one or more mirrors configured to direct the propagation of the first and/or second optical beams.

7. The system of claim 1, wherein the first spectral slicing module further comprises an optical spatial compensator that increases an optical path length traveled by the first optical beam between the first beamsplitter and the second beamsplitter.

8. The system of claim 1, wherein the first spectral slicing module further comprises a compensation filter that corrects a lateral deviation of the first optical beam from the first optical axis of the first spectral slicing module.

9. The system of claim 1, wherein the first and second optical beams propagate along the same direction after being combined into the output optical beam.

10. The system of claim 9, wherein the input optical beam and the output optical beam remain substantially collinear.

11. A method for filtering an input optical beam, comprising:
   splitting the input optical beam into a first optical beam and a second optical beam using a first beamsplitter, wherein the first beamsplitter is a dichroic beamsplitter that substantially transmits the first optical beam and substantially reflects the second optical beam:
   filtering the first optical beam by transmitting the first optical beam through a first spectral slicing module having a first passband, wherein the first spectral slicing module comprises a first longpass filter and a first shortpass filter aligned along a first optical axis, wherein at least one of the first longpass filter or the first shortpass filter is rotatable relative to the first optical axis;
   filtering the second optical beam by transmitting the second optical beam through a second spectral slicing module having a second passband, wherein the second spectral slicing module comprises a second longpass filter and a second shortpass filter aligned along a second optical axis, wherein at least one of the second longpass filter or the second shortpass filter is rotatable relative to the second optical axis, wherein the first and second passbands both include a first range of wavelengths, wherein the first beamsplitter has a transition region that spans a second range of wavelengths, and wherein the second range of wavelengths is narrower than the first range of wavelengths; and
   combining the first and second optical beams into an output optical beam using a second beamsplitter.

12. The method of claim 11, further comprising tuning at least one of a bandwidth or a center wavelength of the first passband by rotating at least one of the first longpass filter or the first shortpass filter.

13. The method of claim 11, further comprising blocking wavelengths of the first optical beam outside the first passband using a blocking filter.

14. The method of claim 11, further comprising increasing an optical path length traveled by the first optical beam between the first beamsplitter and the second beamsplitter using at least one optical spatial compensator.

15. The method of claim 11, further comprising correcting a lateral deviation of the first optical beam from the first optical axis of the first spectral slicing module using at least one compensation filter.

16. A method for configuring an imaging system, comprising:
   splitting an input optical beam into a first optical beam and a second optical beam using a first beamsplitter, wherein the first beamsplitter is a dichroic beamsplitter that substantially transmits the first optical beam and substantially reflects the second optical beam:
   filtering the first optical beam by transmitting the first optical beam through a first spectral slicing module having a first passband, wherein the first spectral slicing module comprises a first longpass filter and a first shortpass filter aligned along a first optical axis, wherein at least one of the first longpass filter or the first shortpass filter is rotatable relative to the first optical axis;
   filtering the second optical beam by transmitting the second optical beam through a second spectral slicing module having a second passband, wherein the second spectral slicing module comprises a second longpass filter and a second shortpass filter aligned along a second optical axis, wherein at least one of the second longpass filter or the second shortpass filter is rotatable relative to the second optical axis, wherein the first and second passbands both include a first range of wavelengths, wherein the first beamsplitter has a transition region that spans a second range of wavelengths, and wherein the second range of wavelengths is narrower than the first range of wavelengths: and
   combining the first and second optical beams into an output optical beam using a second beamsplitter.

17. The method of claim 11, wherein the second beamsplitter is a dichroic beamsplitter.

18. The method of claim 16, wherein the second beamsplitter is a dichroic beamsplitter.

19. The method of claim 16, further comprising tuning at least one of a bandwidth or a center wavelength of the first passband by rotating at least one of the first longpass filter or the first shortpass filter.

20. The method of claim 16, further comprising blocking wavelengths of the first optical beam outside the first passband using a blocking filter.

* * * * *